United States Patent [19]

Accorti, Jr. et al.

[11] Patent Number: 5,810,887

[45] Date of Patent: Sep. 22, 1998

[54] TEMPORARY CATHETER

[75] Inventors: Peter R. Accorti, Jr., Jacksonville; Richard Luceri, Lighthouse Point, both of Fla.; Steven E. Scott, Shorewood, Minn.

[73] Assignee: Rhythm Technologies, Inc., Jacksonville, Fla.

[21] Appl. No.: 817,763

[22] PCT Filed: Aug. 23, 1996

[86] PCT No.: PCT/US96/13969

§ 371 Date: Apr. 24, 1997

§ 102(e) Date: Apr. 24, 1997

[87] PCT Pub. No.: WO97/07835

PCT Pub. Date: Mar. 6, 1997

Related U.S. Application Data

[60] Provisional application No. 60/019,835 Jun. 17, 1996, and 60/002,815 Aug. 25, 1995.

[51] Int. Cl.$^6$ ..................................................... A61N 1/05
[52] U.S. Cl. ............................................................ 607/122
[58] Field of Search .................................... 607/122–128; 128/642; 600/373–381

[56] References Cited

U.S. PATENT DOCUMENTS

| | | |
|---|---|---|
| 3,416,533 | 12/1968 | Fisher et al. ............................. 607/122 |
| 4,154,247 | 5/1979 | O'Neill ..................................... 607/125 |
| 4,662,377 | 5/1987 | Heilman et al. . |
| 4,774,952 | 10/1988 | Smits . |
| 4,957,110 | 9/1990 | Vogel et al. . |
| 4,974,588 | 12/1990 | Smits . |
| 5,005,587 | 4/1991 | Scott . |
| 5,165,403 | 11/1992 | Mehra . |
| 5,170,802 | 12/1992 | Mehra . |
| 5,224,476 | 7/1993 | Ideker et al. . |
| 5,224,491 | 7/1993 | Mehra . |
| 5,306,252 | 4/1994 | Yutori et al. . |
| 5,308,324 | 5/1994 | Hammerslag et al. . |
| 5,327,905 | 7/1994 | Avitall . |
| 5,415,653 | 5/1995 | Wardle . |
| 5,571,163 | 11/1996 | Helland ..................................... 607/123 |
| 5,591,142 | 1/1997 | Van Erp .................................... 607/122 |
| 5,649,974 | 7/1997 | Nelson et al. ............................ 607/122 |

OTHER PUBLICATIONS

"Leads Technology", Peter R. Accorti, Jr., Chapter 8 of *Implantable Cardioverter–Defibrillator*, 1994 (pp. 179–206).

"Shocking Electrode Length Studies", (research note publication) *Atrial Defibrillation*, 1994 InControl, Inc., Redmond, WA.

*Primary Examiner*—Jeffrey R. Jastrzab
*Attorney, Agent, or Firm*—Leydig, Voit & Mayer, Ltd.

[57] ABSTRACT

A catheter includes a torque transmission assembly coupled to an elongate body and an electrical connector wherein the torque transmission assembly can transmit torque and electrical current along the elongate body.

51 Claims, 3 Drawing Sheets

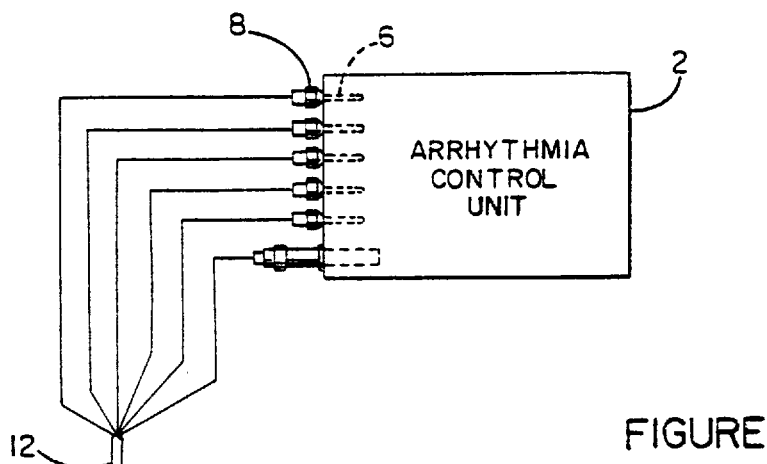
FIGURE 1
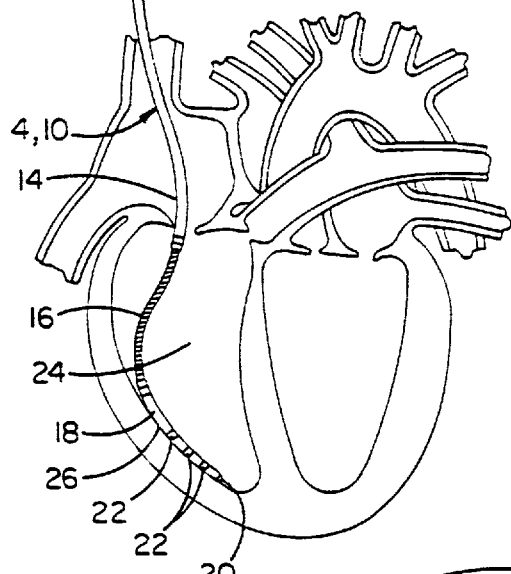
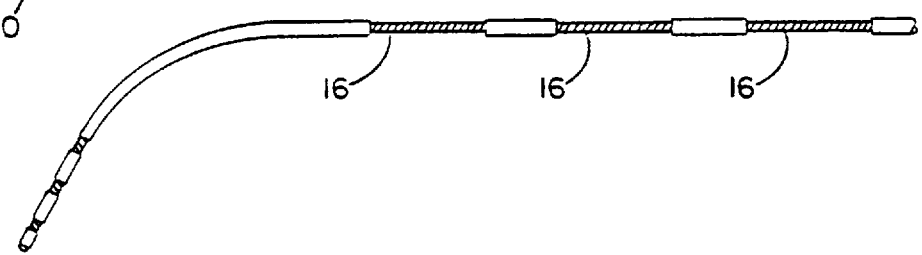
FIGURE 7
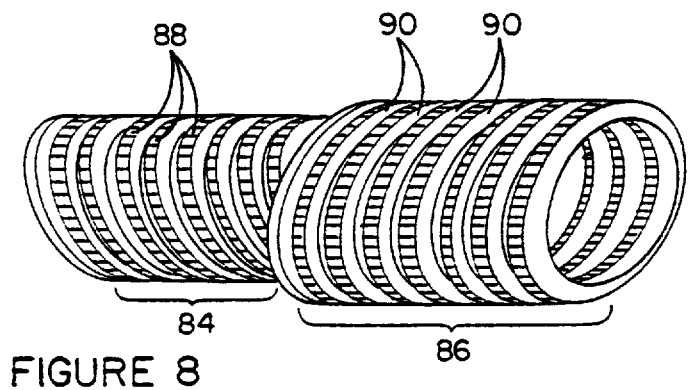
FIGURE 8

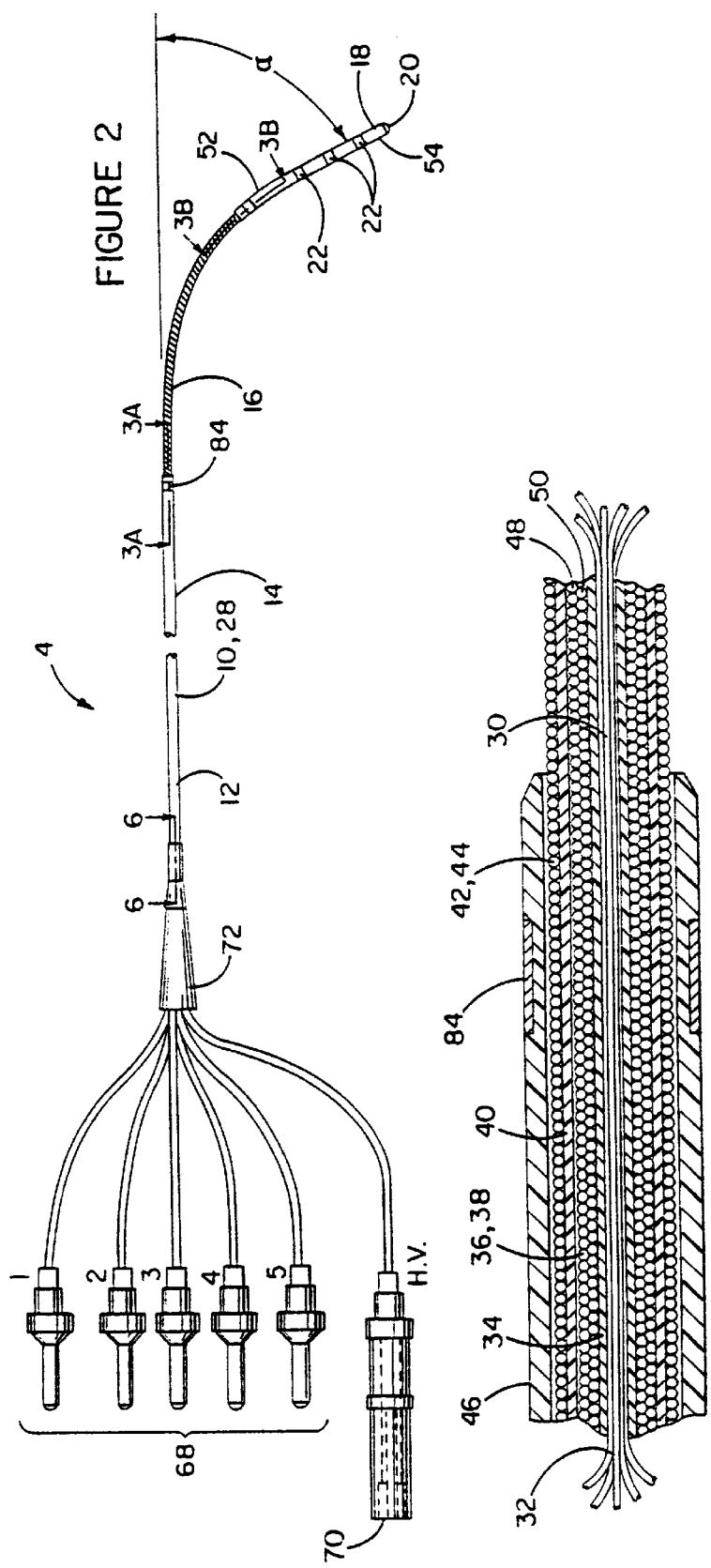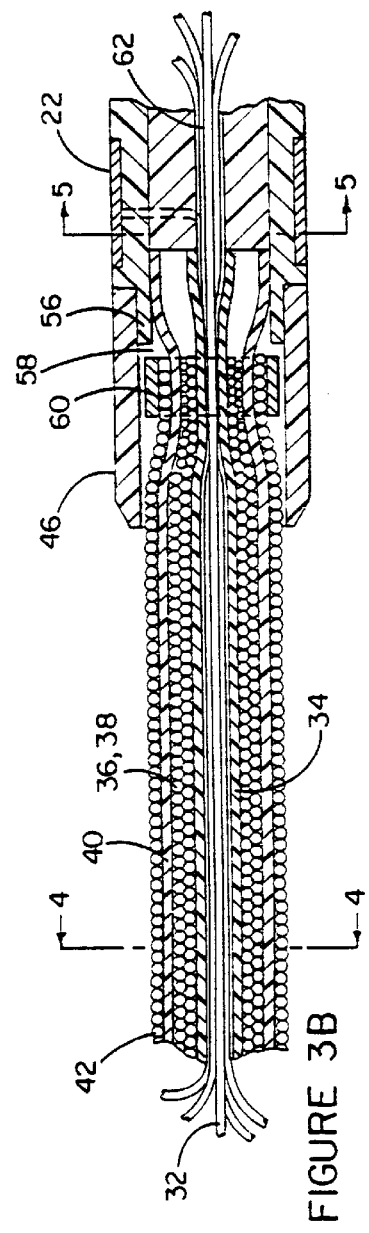

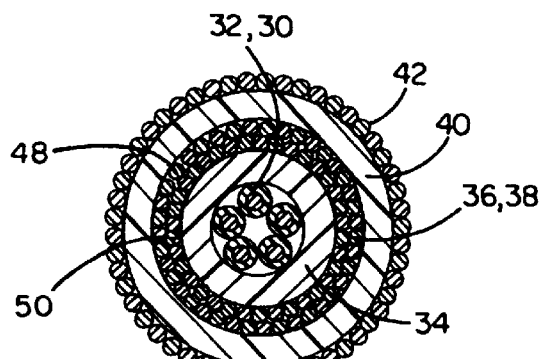
FIGURE 4
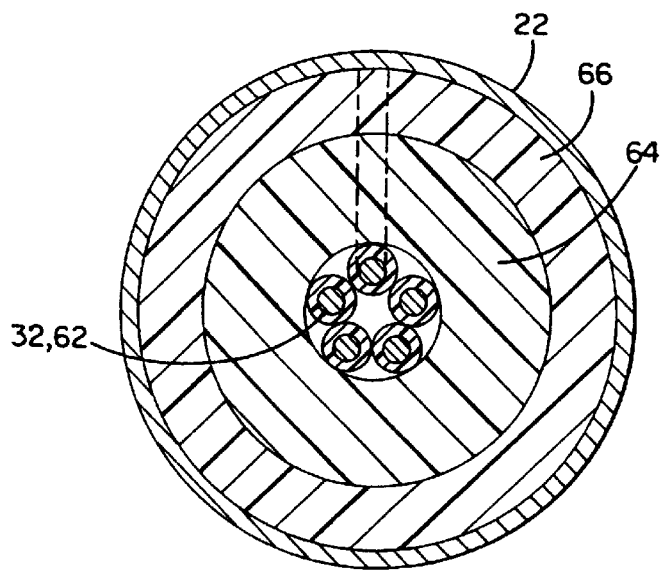
FIGURE 5
FIGURE 6
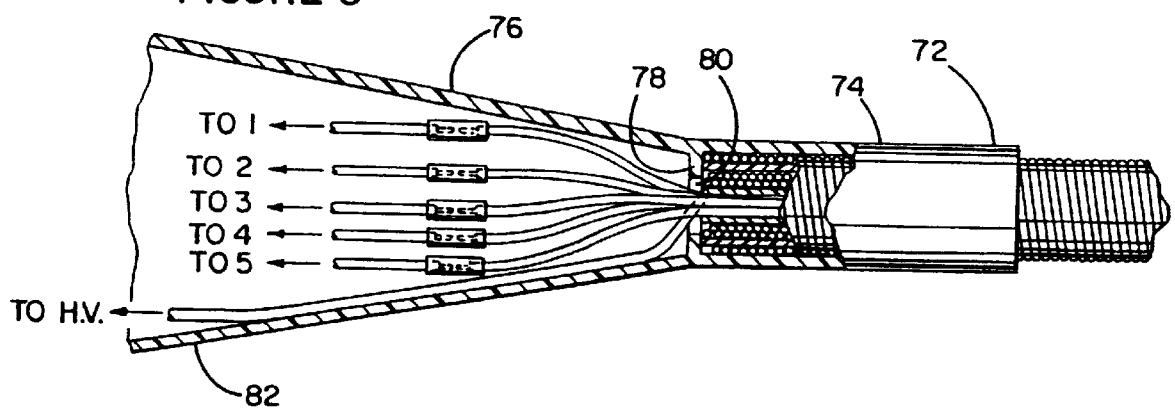

TEMPORARY CATHETER

This application claims priority to U.S. Provisional Patent Application No. 60/002,815, filed Aug. 25, 1995, and to U.S. Provisional Patent Application No. 60/019,835, filed Jun. 17, 1996.

TECHNICAL FIELD

This invention relates to a disposable catheter for temporary insertion into the body, for example, through a venepuncture, and more specifically, to a diagnostic electrophysiology catheter which can diagnose underlying cardiac arrhythmias and can treat the diagnosed arrhythmias by stimulating the human heart with pacing, cardioversion, defibrillation, and/or radiofrequency ablation energies.

BACKGROUND ART

The human heart is a complex muscular organ which is responsible for pumping blood throughout the body. The heart contains four chambers, namely, the right atrium, the right ventricle, the left atrium, and the left ventricle. Blood enters the right chambers of the heart from veins all over the body, is pumped into the lungs where it becomes saturated with oxygen, and then is pumped into the left ventricle where it is pumped throughout the body.

To accomplish this task, the human heart has "pacemaker cells" which are responsible for the rhythmic contraction of the heart. These pacemaker cells are made of nerve bundles and fibers and consist of several nodes and branches. The atrial contractions are governed by the sino-atrial node. Nerve tracts from the sino-atrial node extend to the atrial-ventricular node at the base of the right atrium. The sino-atrial node and its corresponding nerve tracts are responsible for rhythmic atrial contractions. Large nerve tracts extend from the atrial-ventricular node to the ventricular chambers of the heart. These tracts are called the right and left bundle branches. These nerve fibers extend throughout the ventricles and are responsible for synchronous ventricular contractions. Occasionally, abnormal heart rhythms or contractions can occur due to other cells acting as pacemaker cells or blocking the accessory conduction pathways. These irregular heart rhythms or arrhythmias can be lethal, resulting in strokes and cardiac arrest. Arrhythmias can originate in the atrium resulting in atrial tachyarrhythmias and/or atrial fibrillation which may be a precursor to strokes. Ventricular tachyarrhythmias may result in minimal blood pumping through the heart and may possibly lead to cardiac arrest or ventricular fibrillation, both which can be fatal.

Electrophysiological (EP) testing is typically used to diagnose arrhythmias in a patient and this testing involves the passing of several diagnostic EP catheters into the right side of the heart. These EP catheters typically include several sensing rings and a distal tip electrode for the delivery of low energy pacing pulses directly to the heart. The electrical signals of the heart are sensed with the ring electrodes and once an aberrant pathway is determined, low energy pacing pulses are applied to the heart tissue at various intervals or frequencies in order to induce or start the arrhythmia. Once the arrhythmia is induced, it must be terminated and this termination of the arrhythmia is typically accomplished by delivering a high energy defibrillation shock across the patient's chest (transthoracic shocks) with paddles. A specific very high voltage or voltage gradient, namely, a therapeutic voltage, is required within the heart to terminate the induced arrhythmias. Since the thoracic cavity and the skin dissipate much of the applied voltage through resistance, the voltage delivered through a transthoracic defibrillator paddle is substantially greater than the necessary therapeutic voltage in order to compensate for the energy losses through the skin and the thoracic cavity and to ensure that the necessary therapeutic voltage does reach the heart. Unfortunately, the delivery of these external shocks are painful to the patient because these external shocks produce skin burns and, since these external shocks are not directly applied to the heart, a misalignment of the paddles may also result in insufficient voltage reaching the heart which may necessitate the need for yet additional, painful, external shocks.

Once the presence of arrhythmia has been determined, it can be treated and one method of treating the arrhythmia is an arrhythmia control system. Early arrhythmia control systems employed two different sets of electrodes, one set to sense the onset of arrhythmia and a second set to treat the arrhythmia. The first set of electrodes were known as rate sensing electrodes while the second set of electrodes were known as epicardial patch electrodes. Both the rate sensing and epicardial patch electrodes were anchored directly onto the outer surface of the heart and both electrodes required a major surgery under general anesthesia in order to insert them into a patient.

For this reason, epicardial patch electrodes were replaced with transvenous catheters which combined the functions of both the rate sensing and epicardial electrodes into one catheter having a long tubular body and a plurality of electrodes on a distal portion. With a transvenous electrode, no major surgery with general anesthesia was required. Instead, a doctor inserted the distal portion of the catheter into a patient's vein and then torqued and pushed a substantial segment of the tubular body into the vein so that the distal portion of the catheter containing the electrodes was guided along the vein and precisely located within the patient's heart for sensing and then treating the arrhythmia.

An example of a current transvenous catheter is U.S. Pat. No. 5,005,587 which is hereby incorporated by reference for its teaching on an endocardial defibrillation and pacing catheter. This endocardial defibrillation and pacing catheter includes an elongated hollow polyurethane tube with a proximal portion and a distal portion wherein the distal portion includes a distal tip electrode, a plurality of ring electrodes, and a surface braid electrode. Although providing good stiffness and biocompatability, the polyurethane tube lacked sufficient translation between the rotational and displacement forces applied along the body of the polyurethane tube and the corresponding rotational and displacement forces resulting in the distal portion. Instead, only a small fraction of the rotational and displacement forces provided along the body of the polyurethane tube was translated to rotational and displacement forces at the distal portion. The remainder, the majority of the rotational and displacement forces provided along the body of the polyurethane tube, merely caused an accumulation of stress in the polyurethane tube. If sufficient stress was accumulated, the polyurethane tube also tended to buckle or form helices and thereby not allowing the distal portion to reach the precise location within the patient's heart.

SUMMARY OF THE INVENTION

With the foregoing in mind, it is an object of the present invention to provide a catheter which can translate a substantial fraction of the rotational and displacement forces applied along the body of the catheter to rotational and displacement forces at the distal portion of the catheter.

It is another object of the present invention to provide a catheter which can translate a substantial fraction of the rotational and displacement forces applied along the body of the catheter to rotational and displacement forces at the distal portion of the catheter and can also conduct electrical current between the proximal portion and at least one of the distal portion and the one or more exposed segments of the catheter.

It is another object of the present invention to provide a catheter that is flexible, is of relatively small diameter, and can deliver current through one or more exposed segments without the need for special connections, couplers, and/or separate conductor wires.

It is another object of the present invention to provide a flexible catheter wherein the one or more wires in the one or more exposed segments have a large effective surface area.

It is another object of the present invention to provide a transvenous catheter primarily for subcutaneous use which provides current to a precisely controlled location.

It is yet another object of the present invention to provide a diagnostic EP catheter that can sense the heart, can apply pacing pulses to the heart, and can then apply cardioversion, defibrillation, and/or radiofrequency ablation energies to the heart.

One or more of the foregoing objects are achieved in a catheter that includes a torque transmission assembly coupled to an elongate body and an electrical connector wherein the torque transmission assembly can transmit torque and electrical current along the elongate body.

According to one aspect of the invention, the catheter comprises an elongate body, a torque transmission assembly, and an electrical connector. The elongate body includes a distal portion and an opposite proximal portion. The torque transmission assembly includes one or more wires extending along the elongate body from the proximal portion toward the distal portion and one or more exposed segments along the elongate body. The electrical connector is coupled to the wires and these wires can conduct electrical current between the electrical connector and the one or more exposed segments. When inserted within a human body, these wires can also conduct electrical current between the electrical connector and the human body via the exposed wires in the one or more exposed segments of the torque transmission assembly.

According to another aspect of the invention, the catheter comprises an elongate body, a torque transmission assembly, and an electrical connector. The elongate body includes a distal portion and an opposite proximal portion. The torque transmission assembly includes a plurality of first wires, a plurality of third wires, and one or more exposed segments along the elongate body. The plurality of third wires extends along the elongate body from the proximal portion toward the distal portion. The plurality of first wires extends along the elongate body from the proximal portion toward the distal portion and the one or more exposed segments. The electrical connector is coupled to the plurality of first wires and these first wires can conduct electrical current between the electrical connector and the one or more exposed segments. When inserted within a human body, the plurality of first wires can also conduct electrical current between the electrical connector and the human body via the exposed first wires in the one or more exposed segments.

In various embodiments, the one or more wires of the torque transmission assembly can be disposed along the elongate body in a variety of manners. For example, the one or more wires of the torque transmission assembly may be helically wound along the elongate body. Alternatively, the one or more wires of the torque transmission assembly may be braided along the elongate body. Collectively, the wires of the torque transmission assembly ensure that a substantial fraction of the rotational and displacement forces provided along the elongate body are translated to rotational and displacement forces at the distal portion. This allows a doctor to easily push the distal portion of the catheter along a patient's vein and to precisely locate the distal portion within the patient's heart without a stylet to guide the catheter. The wires of the torque transmission assembly also ensure that electrical current can flow between the electrical connector and at least one of the distal portion and the one or more exposed segments and, when inserted within the body, between the electrical connector and the body via the exposed wires in the exposed segments. This allows the catheter to be used in conjunction with, for example, an arrhythmia control system to provide cardioversion, defibrillation, and/or radiofrequency ablation energies to a precise location within a human heart.

An advantage of the catheter according to the present invention over those presently in use is the ability to use different types of assemblies on the distal portion. For example, in the exemplary embodiment, the catheter has secured to the distal portion or the elongate body a pacing and sensing assembly which can sense and pace precise locations within the human heart. Alternatively, in another exemplary embodiment, the catheter could also have secured to the distal portion of the elongate body a floating inflatable and deflatable balloon apparatus. This ability to use different types of assemblies in conjunction with the catheter enhances the catheter's versatility because the catheter can be used in many more different types of treatments than those catheters presently in use.

Other objects and advantages of this invention will become apparent from the detailed description that follows. It should be understood, however, that the detailed description and specific embodiments are provided for illustration only since various additions and modifications within the spirit of the invention will become apparent to those skilled in the art from this disclosure.

BRIEF DESCRIPTION OF THE DRAWINGS

FIG. 1 is a cutaway view of a human heart with a catheter according to the present invention implanted therein;

FIG. 2 is a side view of a catheter according to the present invention;

FIG. 3A is an enlarged cross-sectional view in the direction of line 3A—3A of the catheter shown in FIG. 2;

FIG. 3B is an enlarged cross-sectional view in the direction of line 3B—3B of the catheter shown in FIG. 2;

FIG. 4 is a cross-sectional view in the direction of line 4—4 of the catheter shown in FIG. 3B;

FIG. 5 is a cross-sectional view in the direction of line 5—5 of the catheter shown in FIG. 3B;

FIG. 6 is an enlarged cross-sectional view in the direction of line 6—6 of the catheter shown in FIG. 2;

FIG. 7 is a side view of another catheter according to the present invention with a plurality of exposed segments; and FIG. 8 is an enlarged side view of an exposed segment of a catheter according to the present invention with an alternating plurality of insulated and noninsulated wires.

DESCRIPTION OF PREFERRED EMBODIMENT(S)

FIG. 1 is a cutaway view of the human heart in which a catheter according to the teachings of the present invention has been implanted and used in conjunction with a control unit such as an external arrhythmia control unit 2. The external arrhythmia control unit 2 includes sensing and detecting circuitry, as well as cardioverter, defibrillator, and ablation circuitry, the outputs of which are all coupled to a catheter 4 of the present invention. The external arrhythmia control unit 2 senses an arrhythmic condition of the heart, and in response thereto, emits cardioverting, defibrillating, and/or ablating energies to the heart through the implanted catheter 4 according to the teachings of the present invention. The arrhythmia control unit 2 includes a plurality of receptacles 6 and, coupled to the arrhythmia unit 2, via a plurality of electrical connectors 8 is the catheter 4 of the present invention. The catheter 4 includes an elongate body 10 which has a proximal portion 12, an opposite distal portion 14, and at least one exposed segment 16. A pacing and sensing assembly 18 may be attached to the distal portion 14 of the elongate body 10 and includes a tip electrode 20 and a plurality of ring electrodes 22.

The catheter can be inserted intravenously through a variety of venipuncture sites including the femoral, the sub-clavian, the jugular, and the brachial vein because of its' very small diameter. For example, the catheter 4 shown in FIGS. 1–6 has a diameter of 6 French (F) or less and is typically inserted intravenously through a venipuncture site in the arm or leg. (The French scale is the scale used to denote the sizes of catheters, each French scale being approximately equivalent to 0.33 millimeters in diameter.) After insertion into a vein, rotational and displacement forces provided along the elongate body 10 push the distal portion 14 of the catheter 4 and the pacing and sensing assembly 18 through the vein and into the heart. One or more radio-opaque marker bands 84 located near each exposed segment 16 then allows for the exact placement of the catheter 4 within the heart. For example, as illustrated in FIG. 1, the exposed segment 16 can be positioned within the right ventricle 24 of the heart and the tip and ring electrodes 20, 22 can be positioned in the right ventricle apex 26 of the heart. It should also be appreciated that FIG. 1 is only a single embodiment illustrating a specific use for the catheter of the present invention and that the catheter can be used for a broad range of different procedures and treatments, depending on the specifications of the catheter and the nature of the assembly secured to the distal portion.

In one of the most simple embodiments of the present invention, a catheter according to the teachings of this invention includes a torque transmission assembly coupled to an elongate body wherein the torque transmission assembly can transmit torque along the elongate body. The elongate body includes a distal portion and an opposite proximal portion. The torque transmission assembly includes one or more wires extending along the elongate body and one or more exposed segments along the elongate body. The torque transmission assembly ensures that a substantial fraction of the rotational and displacement forces provided along the elongate body are translated to rotational and displacement forces at the distal portion. An electrical connector is coupled to the wires and these wires can conduct electrical current between the electrical connector and at least one of the distal portion and the one or more exposed segments.

In other embodiments of the present invention, the torque transmission assembly of a catheter according to the teachings of this invention may include a plurality of wires extending along the elongate body from the proximal portion to the distal portion; a plurality of wires and a plurality of different insulation layers, both extending along the elongate body from the proximal portion to the distal portion; a plurality of wires, each plurality of wires being disposed though an insulation layer, and a plurality of different insulation layers, both the plurality of wires and the plurality of insulation layers extending along the elongate body from the proximal portion to the distal portion; and/or a plurality of different wires, each wire in the plurality of wires being bare, partially insulated, or completely insulated, and a plurality of different insulation layers, both the plurality of wires and insulation layers extending along the elongate body from the proximal portion to the distal portion. In each embodiment, the torque transmission assembly of a catheter according to the teachings of this invention ensures that (1) a substantial fraction of the rotational and displacement forces provided along the elongate body are translated to rotational and displacement forces at the distal portion and that (2) electrical current can be conducted between the proximal portion and at least one of the distal portion and the one or more exposed segments in the elongate body.

The torque transmission assembly of a catheter according to the present invention may have one or more exposed segments along the elongate body. As will be discussed more fully below, FIGS. 2–6 illustrate an embodiment of the present invention wherein the torque transmission assembly includes only one exposed segment 16 along the elongated body. Alternatively, the torque transmission assembly may include a plurality of exposed segments 16, as illustrated in FIG. 7.

An embodiment of a catheter 4 according to the teachings of this invention is shown generally in FIGS. 2–6 where like numerals designate previously described elements. In this embodiment, the catheter 4 includes a torque transmission assembly 28 coupled to the elongate body 10 wherein the torque transmission assembly can transmit torque along the elongate body. The elongate body 10 includes a distal portion 12, an opposite proximal portion 14, and one or more insulation layers while the torque transmission assembly 28 includes a plurality of different wires, each plurality of wires preferably being disposed through an insulation layer.

As best shown in FIGS. 3A and 4, the torque transmission assembly 28 of the present invention includes a central region 30 that has a plurality of second wires 32 extending from beyond the distal portion 14 to beyond the proximal portion 12. A second insulation layer 34 is disposed over the plurality of second wires 32 and along the elongate body 10 from the distal portion 14 to the proximal portion 12 to provide electrical and environmental isolation for the plurality of second wires 32. A plurality of third wires 36 are disposed over the second insulation layer 34 and are disposed along the elongate body 10 from the distal portion 14 to the proximal portion 12. The plurality of third wires 36 are preferably extruded through a fifth insulation layer 38 according to any known fabrication process and the fifth insulation layer 38 extends from the distal portion 14 to the proximal portion 12. A first insulation layer 40 is disposed over the plurality of third wires 36 and along the elongate body 10 from the distal portion 14 to the proximal portion 12 to provide electrical and environmental isolation for the plurality of third wires 36. A plurality of first wires 42 are disposed over the first insulation layer 40 and are extruded through a fourth insulation layer 44 according to any known fabrication process. The plurality of first wires 42 are preferably disposed along the elongate body 10 from the proximal portion 12 to the distal portion 14 but may be disposed along a lesser length of the elongate body, i.e., from the proximal portion 12 to the exposed segment 16. The fourth insulation layer 44 extends from the distal portion 14 to the proximal portion 12 but with the exception of the exposed segment 16 of the torque transmission assembly 28 where one or more of the plurality of first wires 42 are bare and exposed to the outside environment. A third insulation layer 46 is disposed over the plurality of first wires 42 and along the elongate body 10 from the distal portion 14 to the proximal portion 12 with the exception of the exposed segment 16 of torque transmission assembly 28 which exposes the one or more of the plurality of first wires 42 to the outside environment. The third insulation layer 46 also provides the catheter 4 with electrical and environmental isolation from the outside environment.

In accordance with one or more aspects of the invention, the plurality of different wires of the torque transfer assembly can be disposed along the elongate body in a variety of manners. For example, the plurality of different wires of the torque transmission assembly may be braided along the elongate body, as will be explained more fully below. Alternatively or additionally, as will be explained more fully below, the plurality of different wires of the torque transmission assembly may be helically wound along the elongate body. Whether braided or helically wound, the plurality of wires of the torque transmission assembly ensures that a substantial fraction of the rotational and displacement forces provided along the elongate body are translated to rotational and displacement forces at the distal portion. This allows a doctor to easily push the distal portion of the catheter through a patient's vein and to precisely locate the distal portion within the patient's heart without a stylet to guide the catheter. The plurality of different wires of the torque transmission assembly also ensures that electrical current can flow between the electrical connector and at least one of the distal portion or the one or more exposed segments and, when inserted within the body, between the electrical connector and the body via the exposed wires in the exposed segments of the torque transmission assembly. This allows the catheter to be used in conjunction with, of example, an arrhythmia control system to provide cardioversion, defibrillation, and/or radiofrequency ablation energies to a precise location within a human heart.

In the embodiment of the catheter 4 illustrated in FIG. 3A and 3B, the torque transmission assembly 28 includes the plurality of first wires 42 and the plurality of third wires 36 which are both helically wound along the elongate body 10 with a pitch angle between 1 degree and 179 degrees. In this application, the pitch angle means the angle which is formed between the elongate body 10 and each wire in the plurality of different wires as the wire is being wound along the elongate body 10. Generally, a pitch angle of between 1 degree and 90 degrees is known in the art as a counter-clockwise helical rotation while a pitch angle of between 91 degrees and 179 degrees is known in the art as a clockwise helical rotation. The plurality of first wires 42 are comprised of between 1 to 100 individual wires and, more preferably, between 20 to 60 individual wires, with each wire having a diameter in the range between 0.0005 inch to 0.020 inch and, more preferably, between 0.002 inch to 0.010 inch. The plurality of third wires 36 are also comprised of between 1 to 100 wires and, more preferably, between 20 to 60 individual wires, with each wire having a diameter in the range between 0.0005 inch and 0.020 inch and, more preferably, between 0.002 inch to 0.010 inch. In the embodiment illustrated in FIGS. 2–6, the plurality of first wires 42 and the plurality of third wires 36 complete one revolution around the elongate body 10 in approximately between 0.23 inch to 0.95 inch. The number of wires, the pitch angles, the diameter, and the material of the wires in the plurality of wires largely determines the torque translation characteristics of the catheter. Accordingly, by varying these criteria above, a catheter can be fabricated according to the teachings of this invention to have any one of a wide range of torque transmission characteristics.

In the embodiment illustrated in FIGS. 2–6, the plurality of first wires 42 and the plurality of third wires 36 are typically any metal, polymer, composition, or alloy that is sufficiently conductive, has sufficient fatigue strength (flexibility) and mechanical strength (tensile and elongation properties), and is sufficiently biocompatible and biostable in the human body to transmit torque and electrical current along the elongate body 30. For example, in the catheter 4 shown in FIGS. 2–6, the plurality of first wires are preferably a titanium alloy but can also be titanium, platinum, and/or platinum alloy. The plurality of third wires may have many of the same characteristics as the plurality of first wires. However, in the embodiment shown in FIGS. 2–6, the plurality of third wires 36 ate not coupled to an electrical connector so they may be less conductive than the plurality of first wires 42. The plurality of the third wires 36 are preferably stainless steel. Typically, the plurality of first wires 42 and the plurality of third wires 36 are helically wound in the same direction, but can also be wound in opposite directions. The plurality of third wires 36 can also be separated into a plurality of fourth wires 48 and a plurality of fifth wires 50 which can be wound in the same or opposite directions in different radii.

As an alternative or in addition to extruding the plurality of wires through an insulation layer, one or more of the individual wires in the plurality of different wires of the torque transmission assembly can be selectively and even partially insulated along its' length depending on the configuration of the catheter. For example, in an embodiment of a catheter similar to the one illustrated in FIGS. 2–6, each wire in the plurality of first wires can be partially insulated dependant on the number of exposed segments in the torque transmission assembly and the energy density required in each exposed segment. For example, the plurality of first wires may be divided into a number of groups which correspond directly with the number of exposed segments in the torque transmission assembly. Each group includes a number of first wires and each group is associated with a specific exposed segment. Each individual wire in each group is insulated from the proximal portion to the distal portion including all the exposed segments in the torque transmission assembly except for the associated exposed segment. In the exposed segment, the individual wires of the group are uninsulated or bare. If a linear decreasing energy density in the exposed segments from the proximal portion to the distal portion is preferred, then each group of first wires may have approximately an equal number of first wires. Alternatively, if a constant energy density throughout all the exposed segment in the catheter is preferred, then the group associated with the exposed segment closest to the proximal portion may have the fewest number of first wires, the groups associated with the exposed segments that are progressively farther away from the proximal portion may have progressively more first wires, and the group associated with the exposed segment farthest from the proximal portion may have the most of first wires. Similarly, one or more of the individual wires in the plurality of third wires can be either insulated or uninsulated dependant, for example, on the number of electrical connections that an assembly attached to the distal portion of the elongate body requires. If the assembly has a large plurality of signal, power, or control lines and/or does not have the plurality of second wires, then some or all of the plurality of third wires can be insulated and can extend beyond the distal portion so as to provide the necessary number of electrical connections between the assembly and any apparatus located beyond the proximal portion of the catheter.

Alternatively, according to the teaching of this invention, the plurality of wires disposed within the exposed segments of the torque transmission assembly may include various sequences of insulated wires and non-insulated wires. For example, in the embodiment illustrated in FIG. 8, the plurality of wires of the torque transmission assembly disposed in the exposed segment includes a first group 84 with a clockwise helical rotation and a second group 86 with a counter clockwise helical rotation disposed around the first group 84 wherein the first group 84 and the second group 86 both may include an alternating plurality of insulated wires 88 and a plurality of non-insulated wires 90. Alternatively, the first group 84 and the second group 86 may also include any sequence of insulated and non-insulated wires. The plurality of insulated wires 88 can be used for providing current to other exposed segments or to the assembly secured to the distal portion of the catheter. Similarly, the plurality of non-insulated wires 90 can be used for the sensing of the heart, the delivery of energy to the heart, or both the sensing of and the delivery of energy to the heart. For example, if the plurality of non-insulated wires includes six individual non-insulated wires, then four of these wires could be used for the delivery of ablation energy to the heart while the remaining two wires could be used as sensing electrodes where one of the remaining wires is of a first polarity and the remaining wire is of opposite second polarity. As can be seen from the various embodiments, the plurality of wires in the torque transmission assembly according to the teaching of this invention may be used for the sensing of the heart, the delivery of energy to the heart, both the sensing of and the transmission of energy to the heart, and/or the transmission of energy or signals to other exposed segments and/or to the assembly attached to the distal portion of the catheter.

An advantage of a catheter according to the teaching of the present invention over those presently in use is the ability to use different types of assemblies on the distal portion of the elongate portion. For example, a catheter according to the teaching of this invention could have secured to the distal portion a floating inflatable and deflatable balloon apparatus. Alternatively, as shown in FIG. 2, the catheter 4 can have secured to the distal portion 14 of the elongate body 10 a pacing and sensing assembly 18 which can sense the heart and apply pacing energy to precise locations within the human heart. The pacing and sensing assembly 18 has a proximal portion 52 and an opposite distal portion 54 and includes a tip electrode 20 disposed on the distal end of the distal portion 54 and a plurality of ring electrodes 22 disposed in a positional relationship with the tip electrode 20. As best shown in FIG. 3B, the proximal portion 52 of the pacing and sensing assembly 18 is secured to the distal portion 14 of the catheter 4 by the addition of medical adhesives to, the securing of, and the heat sealing between a cylindrical lip 56 of the pacing and sensing assembly 18 into a corresponding aperture 58 formed between the third insulation layer 46 and the first insulation layer 40 of the elongate body 10.

As best shown in FIGS. 3B and 5, the pacing and sensing assembly 18 includes a central region 62 that has the plurality of second wires 32 extending from the distal portion 54 to beyond the proximal portion 52, as will be explained more fully below. A first insulation layer 64 is disposed over the plurality of second wires 32 from the distal portion 54 to the proximal portion 52 and a second insulation layer 66 is disposed over the first insulation layer 64 from the distal portion 54 to the proximal portion 52. Collectively, the first and second insulation layers 64, 66 provide electrical and environmental isolation for the plurality of second wires 32 within the central region 62 of the pacing and sensing assembly 18 from the outside environment. The insulation layers in the pacing and sensing assembly 18 and the elongate body 10 are chosen from any material that is biostable, biocompatible, flexible, inert, and is a good insulator. For example, the insulation layers in the catheter 4 shown in FIGS. 2–6 are a polyurethane. When attached to an arrhythmia control unit 2, the electrical connectors 32, the plurality of second wires 68, and the tip and ring electrodes 20, 22 can sense the heart for the onset of arrhythmia and can deliver pace energy to the heart to induce arrhythmia. Typically, as best shown in FIG. 2, the distal portion 14 of the catheter 4 and the pacing and sensing assembly 18 may also be pre-shaped into a curve which facilitates the placement of the distal portion 14 and the pacing and sensing assembly 18 into the heart and/or within the vessels.

Each one of the plurality of second wires 32 electrically connects one of the tip and ring electrodes 20, 22 in the pacing and sensing assembly 18 to a corresponding one of a plurality of connectors. For example, in the embodiment of the catheter 4 shown in FIGS. 2–6, there are five electrodes in the pacing and sensing assembly 18 and correspondingly five electrical connectors 68. Physically, the tip and ring electrodes 20, 22 are electrically connected to the electrical connectors 68 by the plurality of second wires 32 which are disposed in the central regions 30, 62 of both the pacing and sensing assembly 18 and the elongate body 10. Typically, as best shown in FIGS. 4 and 5, each of the plurality of second wires 32 is insulated to electrically isolate each second wire from the remaining second wires. According to the teachings of this invention, each group of first wires associated with each exposed segment in the torque transmission assembly may be electrically connected to a high voltage connector. For example, in the embodiment of the catheter shown in FIGS. 2–6, there is only one exposed segment 16 and correspondingly only one high voltage connector 70. When attached to an arrhythmia control unit 2, the high voltage connector 70 and the plurality of first wires 42 in the exposed segment 16, along with another defibrillation electrode (not shown), provide the cardioversion, the defibrillation, and/or the radiofrequency ablation energies to the precise locations within the human heart.

As best shown in FIG. 3B, the catheter 4 includes a crimp 60 which is disposed over the last plurality of helical winds that the plurality of first wires 42 and the plurality of third wires 36 make at the distal portion 14. The crimp 60 ensures that the helically wound plurality of first wires 42 and the helically wound plurality of third wires 36 at the distal portion 14 will not subsequently become unwound. Similarly, as best shown in FIGS. 2 and 6, the catheter 4 includes a cover 72 disposed over the proximal end of proximal portion 12 of the elongate body 10. The cover 72 includes a tubular portion 74 and a conical portion 76 which are separated by an annular ring 78. The proximal portion 12 of the elongate body 10 is disposed in tubular portion 74 so that the proximal end abuts the annular ring 78. Since the tubular portion 74 has a smaller diameter than that of the elongate body 10, this smaller diameter secures the cover 72 to the elongate body 10 while the annular ring 78 ensures that the helically wound plurality of first wires 42 and the helically wound plurality of third wires 36 will not become subsequently unwound. The annular ring 78 includes a central aperture 80 through which the plurality of second wires 32 and the plurality of first wires 42 are disposed to electrically connect the tip electrode 20, the plurality of ring electrodes 22, and the exposed segment 16 to their respective electrical connectors 68, 70. Once through the central aperture 80 and into the conical portion 76, the plurality of first wires 42 are typically pressed or twisted together and also have an insulation layer 82 disposed over their collective outer surface to electrically and physically insulate these wires from the outside environment.

Although the plurality of wires in the embodiment illustrated in FIGS. 2–6 were helically wound, a catheter according to the teaching of this invention can have the plurality of wires in the torque transmission assembly disposed along the elongate body in any manner. One practical manner is to braid (braided design) the plurality of wires along the elongate body while another practical manner is to weave (woven design) the plurality of wires along the elongate body. Typically a standard braid according to this invention consists of multiple wire groups. For example, a 1×16 braided design has 1 wire for 16 groups, all interwoven together. Alternatively, a standard woven design according to this invention consists of multiple, multiple wire groups. For example, a 4×16 woven design represents 16 groups of 4 wires. Both the braided design and the woven design are interwoven along a single diameter of the elongate body with individual wires or groups of wires undulating over and under individual or groups of wires. Typically, the woven design has fewer and smoother undulations because of the greater number of wires in the group whereas the braided design has more and sharper undulations because of the fewer number of wires in the groups. The number of wires in each group, the pitch angles of each group, the diameter of the wires in each group, and the material of the wires in each group largely determine the torque translation characteristics of the resulting catheter. Accordingly, by varying these criteria, a catheter can be fabricated according to the teachings of this invention to have any one of a wide range of torque transmission characteristics.

Both U.S. Provisional Patent Application No. 60/002,815, filed Aug. 25, 1995, and U.S. Provisional Patent Application No. 60/019,835, filed Jun. 17, 1996, are hereby incorporated by reference into this application for their teachings on catheters.

We claim:

1. A catheter or temporary insertion into a patient, the catheter comprising:

an elongate body including a distal portion and an opposite proximal portion and having an open region;

a torque transmission assembly coupled to the elongate body to transmit torque along the elongate body, the torque transmission assembly including at least one first wire extending along the elongate body, at least one segment of the torque transmission assembly having sufficient torque properties for exposing the first wire at the open region of the elongate body, and the torque transmission assembly ensuring that a substantial fraction of the rotational and displacement forces provided along the elongate body are translated to rotational and displacement forces at the distal portion of the elongate body such that the catheter can be inserted into a patient and located within the patient without a stylet to guide the catheter; and an electrical connector coupled to the at least one first wire whereby the first wire can conduct electrical current between the electrical connector and the at least one exposed segment of the torque transmission assembly.

2. The catheter of claim 1 wherein the at least one wire is helically wound along the elongate body.

3. The catheter of claim 1 wherein the at least one wire is braided along the elongate body.

4. The catheter of claim 1 wherein the catheter further comprises a pacing and sensing assembly, the pacing and sensing assembly including a distal portion and an opposite proximal portion, the proximal portion of the pacing and sensing assembly being secured to the distal portion of the elongate body, the distal portion of the pacing and sensing assembly including a tip electrode disposed on a distal end of the distal portion and at least one ring electrode disposed in a positional relationship with respect to the tip electrode.

5. The catheter of claim 4 wherein the elongate body and wherein a central region extending between the distal portion and the proximal portion, the pacing and sensing assembly including a plurality of second wires disposed in the central regions of the elongate body and the pacing and sensing assembly extends from the distal portion of the pacing and sensing assembly to the proximal portion of the torque transmission assembly, each second wire having an electrical connector on a first end disposed proximate the proximal portion of the elongate body, each of the second wires being electrically connected to a corresponding one of the tip and ring electrodes on the pacing and sensing assembly.

6. The catheter of claim 4 wherein the distal portion of the elongate body and the pacing and sensing assembly is curved.

7. The catheter of claim 1 wherein the at least one first wire is a plurality of first wires, the torque transmission assembly further comprising of a plurality of third wires extending along the elongate body from the proximal portion to the distal portion.

8. The catheter of claim 7 wherein the plurality of first wires are helically wound along the elongate body with a pitch angle between 1 degree to 179 degrees.

9. The catheter of claim 8 wherein the plurality of first wires comprises of between 1 to 100 wires, each wire having a diameter in the range between 0.0005 inch to 0.020 inch.

10. The catheter of claim 7 wherein the plurality of first wires are braided along the elongate body.

11. The catheter of claim 7 wherein the plurality of third wires are helically wound along the elongate body with a pitch angle between 1 degree to 179 degrees.

12. The catheter of claim 11 wherein the plurality of third wires comprises of between 1 to 100 wires, each wire having a diameter in the range between 0.0005 inch to 0.020 inch.

13. The catheter of claim 7 wherein the plurality of third wires are braided along the elongate body.

14. The catheter of claim 1 wherein the torque transmission assembly further comprises at least one third wire, the at least one third wire being helically wound along the elongate body from the proximal portion toward the distal portion and the at least one first wire being helically wound along the elongate body from the proximal portion toward the distal portion over the at least one third wire, the catheter further comprising an electrode assembly and a connector assembly, wherein the electrode assembly includes a distal portion, a proximal portion mounted to the distal portion of the elongate body, and one or more electrodes and wherein the connector assembly includes the electrical connector and one or more electrode connectors electrically coupled to the exposed segment of the torque transmission assembly and the one or more electrodes of the electrode assembly.

15. The catheter of claim 14 further comprising an inner insulation region and an outer insulation region wherein the inner insulation region extends from the proximal portion toward the distal portion of the elongate body between the at least one helically wound first wire and the at least one helically wound third wire, wherein the outer insulation region extends over the at least one helically wound first wire from the proximal portion toward the distal portion of the elongate body except at the exposed segment of the torque transmission assembly, defining an open region along the elongate body.

16. The catheter of claim 15 wherein the elongate body includes a central region and the electrode assembly includes a central region, one or more second wires extending through the central regions of the elongate body and the electrode assembly connect the one or more electrode connectors of the connector assembly to the one or more electrodes of the electrode assembly, and a second inner insulation region extends between the second wires and at least one helically wound third wire from the proximal portion toward the distal portion of the elongate body.

17. The catheter of claim 16 wherein the at least one helically wound first wire completes one revolution around the elongate body in the range from about 0.23 inch to about 0.95 inch and wherein the catheter has a diameter of about 6 French or less.

18. The catheter of claim 15 wherein the one or more third wires are helically wound along the elongate body, the one or more of the third wires being connected between one or more of the electrode connectors of the connector assembly and the one or more electrodes of the electrode assembly.

19. The catheter of claim 18 wherein the at least one helically wound first wire completes one revolution around the elongate body in the range from about 0.23 inch to about 0.195 inch and wherein the catheter has a diameter of about 6 French or less.

20. The catheter of claim 1 wherein the torque transmission assembly comprises a plurality of first wires helically wound along the elongate body and comprising first and second groups of wires, each wire of the first group being insulated from the proximal portion toward the distal portion of the elongate body except in the first exposed segment where the wire is uninsulated exposing the wire of the first group in the first exposed segment at an open region of the elongate body and each wire of the second group being insulated from the proximal toward the distal portion of the elongate body, the catheter further comprising an inner insulation region, an outer insulation region, an electrode assembly, and a connector assembly, wherein the inner insulation region extends from the proximal portion toward the distal portion of the elongate body, the plurality of first wires being helically wound around the inner insulation region, wherein the outer insulation region extends over the plurality of first wires from the proximal portion toward the distal portion of the elongate body except at the exposed segment of the torque transmission assembly defining the open region along the elongate body, wherein the electrode assembly has a distal portion, a proximal portion mounted to the distal portion of the elongate body, and one or more electrodes, and wherein the connector assembly comprises the electrical connector and one or more electrode connectors electrically coupled to the exposed segment of the torque transmission assembly and the one or more electrodes of the electrode assembly.

21. The catheter of claim 20 wherein the elongate body includes a central region and the electrode assembly includes a central region, one or more second wires extending through the central regions of the elongate body and the electrode assembly connect the one or more electrode connectors of the connector assembly to the one or more electrodes of the electrode assembly.

22. The catheter of claim 20 wherein the wires of the second group are connected between the one or more electrode connectors of the connector assembly and the one or more electrodes of the electrode assembly.

23. The catheter of claim 20 wherein the plurality of helically wound first wires completes one revolution around the elongate body in the range from about 0.23 inch to about 0.95 inch and wherein the catheter has a diameter of 6 French or less.

24. The catheter of claim 1 wherein the torque transmission assembly comprises first and second exposed segments and a plurality of first wires including the at least one first wire, the plurality of first wires being helically wound along the elongate body and comprising first and second groups of wires, each wire of the first group being insulated from the proximal portion toward the distal portion of the elongate body except in the first exposed segment where the wire is uninsulated exposing the wire of the first group in the first exposed segment at an open region of the elongate body and each wire of the second group being insulated from the proximal portion toward the distal portion of the elongate body except in the second exposed segment where the wire is uninsulated exposing the wire of the second group in the second exposed segment at an open portion of the elongate body.

25. The catheter of claim 24 further comprising a connector assembly having a plurality of electrical connectors including one or more electrical connectors coupled to the first and second groups of wires.

26. The catheter of claim 24 further comprising an inner insulation region and an outer insulation region, wherein the inner insulation region extends from the proximal portion toward the distal portion of the elongate body, the plurality of first wires being helically wound around the inner insulation region, and wherein the outer insulation region extends over the plurality of first wires from the proximal portion toward the distal portion of the elongate body except at the exposed segments of the torque transmission assembly, defining one or more open regions along the elongate body.

27. The catheter of claim 26 further comprising an electrode assembly and a connector assembly, wherein the electrode assembly has a distal portion, a proximal portion mounted to the distal portion of the elongate body, and one or more electrodes and wherein the connector assembly comprises the electrical connector and one or more electrode connectors electrically coupled to the exposed segments of the torque transmission assembly and the one or more electrodes of the electrode assembly.

28. The catheter of claim 27 wherein the elongate body includes a central region and the electrode assembly includes a central region, one or more second wires extending through the central regions of the elongate body and the electrode assembly connect one or more of the electrode connectors of the connector assembly to the one or more electrodes of the electrode assembly.

29. The catheter of claim 27 wherein the torque transmission assembly further includes one or more third wires helically wound inside the plurality of first wires along the elongate body from the proximal portion toward the distal portion, the one or more third wires being connected between one or more of the electrode connectors of the connector assembly and the one or more electrodes of the electrode assembly.

30. The catheter of claim 24 wherein the torque transmission assembly comprises a third exposed segment and the plurality of first wires comprises a third group of wires, each wire of the third group being insulated from the proximal portion toward the distal portion of the elongate body except in the third exposed segment where the wire is uninsulated exposing the wire of the third group in the third exposed segment at an open region of the elongate body.

31. The catheter of claim 30 further comprising an inner insulation region and an outer insulation region, wherein the inner insulation region extends from the proximal portion toward the distal portion of the elongate body, the plurality of first wires being helically wound around the inner insulation region, and wherein the outer insulation region extends over the plurality of first wires from the proximal portion toward the distal portion of the elongate body except at the exposed segments of the torque transmission assembly, defining one or more open regions along the elongate body.

32. The catheter of claim 31 further comprising a connector assembly having a plurality of electrical connectors including one or more electrical connectors coupled to the first, second, and third groups of wires, wherein the plurality of helically wound first wires completes one revolution around the elongate body in the range from about 0.23 inch to about 0.95 inch and wherein the catheter has a diameter of about 6 French or less.

33. The catheter of claim 1 further comprising a balloon apparatus secured to the distal portion of the elongate body.

34. A catheter for temporary insertion into a patient, the catheter comprising:
   an elongate body including a distal portion and an opposite proximal portion and having an open region;
   a torque transmission assembly coupled to the elongate body to transmit torque along the elongate body, the torque transmission assembly including a plurality of first wires and a plurality of third wires, at least one segment of the torque transmission assembly exposing the plurality of first wires at the open region of the elongate body, the plurality of third wires extending along the elongate body from the proximal portion toward the distal portion and the plurality of first wires extending along the elongate body from the proximal portion toward the distal portion, and the torque transmission assembly having sufficient torque properties for ensuring that a substantial fraction of the rotational and displacement forces provided along the elongate body are translated to rotational and displacement forces at the distal portion of the elongate body such that the catheter can be inserted into a patient and located within the patient without a stylet to guide the catheter; and
   an electrical connector coupled to the plurality of first wires whereby the plurality of first wires can conduct electrical current between the electrical connector and the at least one exposed segment of the torque transmission assembly.

35. The catheter of claim 34 wherein the catheter further comprises a pacing and sensing assembly, the pacing and sensing assembly including a distal portion and an opposite proximal portion, the proximal portion of the pacing and sensing assembly being secured to the distal portion of the elongate body, the distal portion of the pacing and sensing assembly including a tip electrode disposed on a distal end of the distal portion and at least one ring electrode disposed in a positional relationship with respect to the tip electrode.

36. The catheter of claim 35 wherein the elongate body and the pacing and sensing assembly include a central portion extending between the distal portion and the proximal portion and wherein a plurality of second wires disposed in the central portions of the elongate body and the pacing and sensing assembly extends from the distal portion of the pacing and sensing assembly to the proximal portion of the torque transmission assembly, each second wire having an electrical connector on a first end disposed proximate the proximal portion of the elongate body, each of the second wires being electrically connected to a corresponding one of the tip and ring electrodes on the pacing and sensing assembly.

37. The catheter of claim 36, wherein the elongate body further comprises of a second insulation layer disposed between the plurality of third wires and the plurality of second wires and extending from the proximal portion to the distal portion.

38. The catheter of claim 35 wherein the distal portion of the elongate body and the pacing and sensing assembly is curved.

39. The catheter of claim 36 wherein an insulation layer is disposed on an outer surface of each wire in the plurality of second wires and on a select group of wires in the plurality of first and third wires.

40. The catheter of claim 34 wherein the plurality of third wires are helically wound along the elongate body with a pitch angle between 1 degree and 179 degrees and the plurality of first wires are helically wound along the plurality of third wires with a pitch angle between 1 degree and 179 degrees.

41. The catheter of claim 34 wherein the plurality of first wires are selected from the group consisting of platinum, platinum alloy, titanium, and titanium alloy and the plurality of third wires are stainless steel.

42. The catheter of claim 40 wherein the plurality of first and third wires are helically wound in the same direction.

43. The catheter of claim 34 wherein the plurality of third wires are braided along the elongate body and the plurality of first wires are braided along the plurality of third wires.

44. The catheter of claim 34, wherein the elongate body further comprises of a first insulation layer disposed between the plurality of first wires and the plurality of third wires and extending from the proximal portion to the distal portion.

45. The catheter of claim 34, wherein the elongate body further comprises of a third insulation layer disposed over the plurality of first wires, the third insulation layer extending from the proximal portion to the at least one exposed segment and from the at least one exposed segment to the distal portion.

46. The catheter of claim 34, wherein the plurality of first wires are extruded through a fourth insulation layer, the fourth insulation layer extending from the proximal portion to the at least one exposed segment and from the at least one exposed segment to the distal portion.

47. The catheter of claim 34, wherein the plurality of third wires are extruded through a fifth insulation layer, the fifth insulation layer extending from the distal portion to the proximal portion.

48. The catheter of claim 34, wherein the plurality of first wires comprises of between 1 to 100 wires, each wire having a diameter in the range between 0.0005 inch and 0.020 inch.

49. The catheter of claim 34, wherein the plurality of third wires comprises of between 1 to 100 wires, each wire having a diameter in the range between 0.0005 inch to 0.020 inch.

50. The catheter of claim 40 wherein the plurality of third wires comprises of a plurality of fourth and fifth wires, the plurality of fourth and fifth wires helically wound in opposite directions.

51. The catheter of claim 34 further comprising a balloon apparatus secured to the distal portion of the elongate body.

* * * * *

UNITED STATES PATENT AND TRADEMARK OFFICE
CERTIFICATE OF CORRECTION

PATENT NO. : 5,810,887
DATED : September 22, 1998
INVENTOR(S) : Accorti, Jr. et al.

It is certified that error appears in the above-identified patent and that said Letters Patent is hereby corrected as shown below:

Column 11, Line 47, change "or to --for--;

Line 55-56, delete "having sufficient torque properties for";

Line 58, after "assembly" insert --having sufficient torque properties for--;

Column 12, Line 18, change "wherein" to --the pacing and sensing assembly include--;

Line 19-20, change ", the pacing and sensing assembly including" to --and wherein--;

Line 35, after "comprising" delete --of--;

Line 42, after "comprises" delete --of--;

Line 50, after "comprises" delete --of--;

UNITED STATES PATENT AND TRADEMARK OFFICE
CERTIFICATE OF CORRECTION

PATENT NO. : 5,810,887
DATED : September 22, 1998
INVENTOR(S) : Accorti, Jr. et al.

It is certified that error appears in the above-identified patent and that said Letters Patent is hereby corrected as shown below:

Column 13, Line 19, after "and" insert --the--;

Line 35, change "0.195" to --0.95--;

Line 46, after "proximal" insert --portion--;

Column 16, Line 12, after "comprises" delete --of--;

Line 39, after "comprises" delete --of--;

Line 43, after "comprises" delete --of--;

Line 58, after "comprises" delete --of--;

Line 61, after "comprises" delete --of--;

Line 64, after "comprises" delete --of--.

Signed and Sealed this

Sixteenth Day of March, 1999

Attest:

Q. TODD DICKINSON

Attesting Officer    Acting Commissioner of Patents and Trademarks